United States Patent [19]
Klimmek et al.

[11] Patent Number: 5,610,220
[45] Date of Patent: Mar. 11, 1997

[54] POWDER-FORM POLYMERS WHICH ABSORB, EVEN UNDER PRESSURE, AQUEOUS LIQUIDS AND BLOOD, A METHOD OF PRODUCING THEM AND THEIR USE IN TEXTILE ARTICLES FOR BODY-HYGIENE APPLICATIONS

[75] Inventors: Helmut Klimmek; Helmut Brehm, both of Krefeld, Germany

[73] Assignee: Chemische Fabrik Stockhausen GmbH, Krefeld, Germany

[21] Appl. No.: 464,823

[22] PCT Filed: Dec. 17, 1993

[86] PCT No.: PCT/EP93/03586

§ 371 Date: Jun. 30, 1995

§ 102(e) Date: Jun. 30, 1995

[87] PCT Pub. No.: WO94/15651

PCT Pub. Date: Jun. 21, 1994

[30] Foreign Application Priority Data

Dec. 30, 1992 [DE] Germany .......................... 42 44 548.5

[51] Int. Cl.⁶ ..................................................... C08K 3/32
[52] U.S. Cl. .......................... 524/417; 524/114; 524/108; 524/280; 524/503; 524/547; 524/556; 525/329.8; 525/340; 525/328.2; 525/328.5; 442/417
[58] Field of Search .................................... 524/114, 280, 524/108, 417, 503, 547, 556; 525/329.8, 328.2, 340, 328.5; 428/240, 283

[56] References Cited

U.S. PATENT DOCUMENTS

| | | | |
|---|---|---|---|
| 3,991,018 | 11/1976 | Strop et al. | 525/340 X |
| 4,031,037 | 6/1977 | Kalal et al. | 525/340 X |
| 4,043,952 | 8/1977 | Ganslaw et al. | 526/47 X |
| 4,076,663 | 2/1978 | Masuda et al. | 128/284 X |
| 4,090,013 | 5/1978 | Ganslaw et al. | 526/15 |
| 4,202,815 | 5/1980 | Wegmann | 524/280 X |
| 4,286,082 | 8/1981 | Tsubakimoto et al. | 526/240 |
| 4,497,930 | 2/1985 | Yamasaki et al. | 524/556 |
| 4,500,670 | 2/1985 | McKinley et al. | 524/445 |
| 4,548,847 | 10/1985 | Aberson et al. | 524/417 |
| 5,331,059 | 7/1994 | Engelhardt et al. | 525/340 |
| 5,409,771 | 4/1995 | Dahmen et al. | 524/280 X |

*Primary Examiner*—Judy M. Reddick
*Attorney, Agent, or Firm*—Oblon, Spivak, McClelland, Maier & Neustadt, P.C.

[57] ABSTRACT

The invention relates to powdery cross-linked polymers (superabsorbers) capable of absorbing aqueous liquids and blood, which are formed of 55–99.9%-wt. polymerized unsaturated, polymerizable acid-groups-comprising monomers which are neutralized to the extent of at least 25 mol-%, b) 0–40%-wt. polymerized unsaturated monomers copolymerizable with a), c) 0.1–5.0%-wt. of a cross-linking agent, d) 0–30%-wt. of a water-soluble polymer, whereby the weight amounts of a) to d) relate to anhydrous polymers, characterized in that 100 parts of the particle-shaped polymers have been mixed with an aqueous solution consisting of a maximum of 10 parts of an at least 10% phosphoric acid and a) 0.05–0.3 parts of a compound capable of reacting with at least two carboxyl groups and not comprising an alkali-salt-forming group in the molecule, and/or b) 0.05–1 parts of a compound capable of reacting with at least two carboxyl groups and comprising an alkali-salt-forming group in the molecule, and that they have been heated to 150°–250° C. The superabsorbers according to the invention have a high retention capacity, high gel strength and a high absorption under load and can be manufactured without an organic solvent and with only a small amount of treatment agent for the surface treatment of the powdery polymer. The invention further relates to the use of said polymers in textile constructions for the absorption of body liquids, said constructions preferably consisting of 2 to 80%-wt. superabsorber and the remainder up to 100 of hydrophilic fibers.

16 Claims, No Drawings

POWDER-FORM POLYMERS WHICH ABSORB, EVEN UNDER PRESSURE, AQUEOUS LIQUIDS AND BLOOD, A METHOD OF PRODUCING THEM AND THEIR USE IN TEXTILE ARTICLES FOR BODY-HYGIENE APPLICATIONS

The present invention relates to powdery cross-linked polymers absorbing aqueous liquids and blood (superabsorbers) and having improved properties with regard to swelling and retention capacity for aqueous liquids under load. The present invention further relates to a process for the manufacture of said polymers as well as to the use thereof in absorbent sanitary articles, such as diapers, in the adult incontinence, feminine hygiene, and for wound dressing.

Superabsorbers are water-insoluble, cross-linked polymers which, under swelling and formation of hydrogels, are capable of absorbing large amounts of aqueous and body liquids, such as urine or blood, and of retaining the absorbed amount of liquid under a certain pressure/load. Owing to said characteristic absorption properties the polymers are mainly used for incorporating them into sanitary articles, for example, diapers and sanitary napkins.

The superabsorbers which are commercially available today are cross-linked polyacrylic acids or cross-linked starch-acrylic-acid-graft-polymers the carboxyl groups of which are partially neutralized with sodium hydroxide solution or caustic potash. In principle, the powdery superabsorbers are manufactured by two methods:

According to the first method, partially neutralized acrylic acid in aqueous solution in the presence of a multifunctional cross-linking agent is converted into a gel by radical polymerization, the gel is then crumbled, dried, ground, and screened out to the desired particle size. This polymerization in solution may either be carried out continuously or discontinuously. Typical methods are described, for example, in U.S. Pat. Nos. 4,286,082 and 4,076,663 and German patent No. 27 06 135.

The second method is the inverse suspension or emulsion polymerization. In this process, an aqueous partially neutralized acrylic acid solution is dispersed in a hydrophobic organic solvent by means of protective colloids or emulsifiers, and the polymerization is started by radical initiators. After completion of the polymerization, the water is azeotropically removed from the reaction mixture and the polymeric product filtered off and dried. The cross-linking reaction may be effected by incorporating a polyfunctional cross-linking agent, which is dissolved in the monomer solution, by polymerization, and/or by reacting suitable cross-linking agents with functional groups of the polymer during one of the production steps. The process is described, for example, in U.S. Pat. No. 4,340,706 and German patent Nos. 37 13 601 and 28 40 010.

Initially, only the high swelling capacity on contact with liquids, also referred to as free swelling capacity, had been the main factor in the development of superabsorbers; later it was found, however, that not only the amount of absorbed liquid is of importance but also the stability of the swollen gel. However, absorbency, also referred to as swellability or free swelling capacity, on the one hand, and gel strength of a cross-linked polymer, on the other hand, represent contrary properties; this has been known from U.S. Pat. No. 3,247,171 and U.S. Pat. No. Re 32,649. This means that polymers having a particularly high absorbency exhibit a poor strength of the swollen gel so that the gel is deformable under pressure (e.g., the load of a body) and further liquid distribution and absorption is prevented. According to U.S. Pat. No. Re 32,649 a balanced proportion of such superabsorbers in a diaper construction ensures liquid absorption, liquid transport, and dryness of the diaper and the skin. In this connection, not only the polymer's capacity of retaining a liquid under subsequent pressure, after swelling freely first, is of importance but also the fact that liquids are absorbed even against a simultaneously acting pressure, i.e. during the liquid absorption; this is the case in practice when a baby or person sits or lies on a sanitary article or when shear forces are acting, e.g. by movements of legs. In EP No. 03 39 461 A 1 this special absorption property is referred to as absorption under load.

The only way to meet the increasing trend of reducing the size and thickness of sanitary articles for esthetic and environmental reasons (reduction of waste in the land fill) is to reduce the large-volume fluff pulp portion in diapers and to increase the portion of superabsorber at the same time. For that reason the superabsorber has to take over additional functions with respect to liquid absorption and transport thereof, which previously were performed by the fluff pulp.

If the content of superabsorber in the hygienic article, e.g. a diaper, is increased to 40% or even 60% and more, commercially available superabsorbers virtually turn useless. The liquid absorption, in particular under load, slows down excessively. The particles tend to form a "coagulated gel". The resulting gel barrier blocks the further liquid transport. This phenomenon is known as "gel blocking".

To provide superabsorbing polymers having the special property combination, such as high retention capacity, high gel strength and high absorbency under load, it is necessary to treat the powdery polymers in a subsequent step.

According to GB 21 19 384 A an obvious improvement of the properties is achieved by treating the polymers with compounds having at least two functional groups capable of reacting with the carboxyl groups of the particle shaped polymers in the surface layer.

DE OS 35 23 617 describes a process for the secondary treatment of powdery polymers with a polyvalent alcohol which is applied to the powdery polymer prior to the reaction in an undiluted form or diluted with water and/or an organic solvent at an elevated temperature.

According to DE-PS 40 20 780 the swelling capacity of a superabsorbing polymer against pressure is improved by heating the polymer powder having 0.1 to 5 %-wt. alkylene carbonate which has been applied thereto, optionally diluted with water and/or alcohol.

According to EP 04 50 924 A2 the surface treatment of an absorbing polymer is carried out with a polyol, optionally diluted with water and/or an organic solvent (as is the case in DE OS 35 23 617). This publication thoroughly considers the importance of diluting the treatment agent with water and/or an organic solvent. If the treatment agent which is capable of reacting with the carboxyl groups of the polymer is exclusively diluted with water, considerable process technological difficulties arise. The powdery water-swellable polymer sets up on contact with water or aqueous solutions, rendering a homogeneous distribution of the treatment agent on the particle surface impossible. If the mixing of the water-swellable powdery polymer with a compound capable of reacting with the carboxyl groups of the polymer is effected with water in order to support the diffusion process of the treatment agents into the solid matter, it is absolutely necessary to render the water inert by using an excess of treatment agent or a non-reactive organic solvent. Rendering the water inert by using an organic solvent involves employing liquids which do not swell the polymer, i.e., which do not result in agglomerations during the mixing with the powdery polymer.

Experts know of the difficulty to mix small liquid amounts with powdery substances homogeneously, in particular if each individual particle is to be coated evenly.

Diluting the treatment agent with an organic solvent to a high extent would have positive effects on the distribution of the agent on the surface of the powdery polymer, however, if liquid amounts of more than 1%-wt. are used, a wet polymer powder results plugging the conveyors in continuous processes.

The distribution is improved by increasing the amount of treatment agent to more than 1%-wt., however, a moist tacky powder is obtained. If an amount of water exceeding that necessary to produce an about 50% solution is added to the treatment agent prior to the mixing process, in order to accelerate the diffusion of the treatment agent into the polymer particle, the powdery polymer sets up. In the continuous mixing process of water-swellable polymers with solutions of a treatment agent in a mixer lined with special plastics, which is described in EP 04 50 923 A2, the moist polymer powder is prevented from sticking to the walls of the mixer and the mixing work is reduced but there is no improvement in the behavior of the mixed product.

According to the process of EP-PS 0083022 the secondary treatment of hydrous gel-like polymer particles is carried out in organic solvents. After mechanical separation of the polymer, drying is effected which automatically results in a condensate of water and organic solvent, such as alcohol, hydrocarbon, chlorinated hydrocarbon or ketone, which then has to be processed in such a way that solvent portions do not reach the environment either via the extracted air or via the waste water.

To sum it up, the following conditions result for coating the powdery water-swellable polymer with a substance which is to be brought to reaction in the surface layer of the individual particle:

The amount of treatment agent must suffice to coat the polymer powder evenly.

The amount of water serving as distribution auxiliary and as a carrier for the treating agent into the polymer surface layer is restricted since otherwise irreversible formation of lumps of the polymer particles will result.

The total amount of treatment agent, water and, optionally, organic solvent is restricted since otherwise wet non-flowable mixtures will result.

Considering the mixing process of water-swellable polymers and treatment agent separately from the total process, the use of organic solvents together with the treating agent seems to be most appropriate. The distribution of the treating agent and limited amounts of water on the polymer powder can be achieved reliably. Also, the use of larger amounts of treating agent ensures a good distribution on the polymer—even in the presence of water—if the treatment agent may also take the function of the organic solvent, i.e. prevents the powdery polymer from setting up. However, according to EP 04 50 923 A2, the swelling capacity of the polymer may considerably decrease if the treatment agent is used in excessive amounts.

Even if the mixing process of powdery water-swellable polymers and, optionally, diluting agents, has been conducted in an optimal manner, the effects on the subsequent reaction at elevated temperatures must be taken into consideration. If the improved properties of superabsorbing polymers are achieved by subsequent esterification and/or amidation of the carboxyl groups of the polymer, reaction temperatures of >150° C. are necessary at reasonable reaction times. With these temperatures, in addition to water, which is contained in the starting polymer by 8 to 15%-wt., and solvent, considerable amounts of treating agent are evaporated which have to be removed from the reactor (dryer) to prevent a condensation in the reactor. The selective vapor transport is effected with purge gas, optionally pre-heated, since condensed water vapor would result in formation of lumps and condensed treatment agent would result in formation of lumps and discoloration of the powdery polymer.

Water vapor, evaporating treating agent, oxidation products, residual monomers, as well as other volatile reaction products and organic solvents can only difficultly be removed from the exhaust gas, i.e., they are in the air or waste water necessarily.

Accordingly, it is the object of the present invention to provide superabsorbers which exhibit the property combination of high retention capacity, high gel strength and high absorbency under load and which may be manufactured without using an organic solvent and with only small amounts of treatment agent for the secondary treatment of the powdery polymer.

This object is achieved by the characterizing features of the claims. Most surprisingly, it was found that the use of phosphoric acid as diluting agent for the agent with which the surface of the absorbing resin is treated results in superabsorbers having the desired property combination at a considerable reduction in the amounts of treatment agent.

The phosphoric acid is advantageously used at a maximum amount of 10 parts (all parts given in the following signify parts per weight) per 100 parts of polymer and at a concentration of at least 10%-wt. If only 0.1%-wt. $H_3PO_4$, relative to polymer powder, is used, superabsorbers having the improved properties according to the present invention are obtained.

According to the present invention, as treatment agents are used:

a) 0.05–0.3 parts of a compound capable of reacting with at least two carboxyl groups of the powdery polymer and not comprising an alkali-salt-forming group, preferably polyols, such as ethylene glycol, propanediol, polyethylene glycol, glycerol, and alkylene carbonates, such as ethylene carbonate, and/or b) 0.05–1 parts of a compound capable of reacting with at least two carboxyl groups of the powdery polymer and additionally comprising an acid, alkali-salt-forming group in the molecule, e.g. polyhydroxy carboxylic acids, such as dimethylolpropionic acid (=2,2-bis(hydroxymethyl)propionic acid).

The treatment agents according to a) have the advantage that their volatility during the reaction with the carboxyl groups of the powdery polymer is restricted by salt formation in the surface layer of the polymer.

The water-absorbing polymer which may be used for coating is obtained by polymerizing 55 to 99.9%-wt. of monomers having acid groups, e.g., acrylic acid, methacrylic acid, 2-acrylamido-2-methylpropane sulfonic acid, or mixtures of said monomers; the acid groups are neutralized to the extent of at least 25 mol-% and are present, e.g. as sodium, potassium or ammonium salts. The neutralization degree preferably amounts to about at least 50 mol-%. Particularly preferred is a polymer formed of cross-linked acrylic acid or methacrylic acid which is neutralized to the extent of 50 to 80 mol-%.

Further monomers suitable for the production of the water-absorbing polymers include 0 to 40%-wt. acrylamide, methacrylamide, hydroxyethyl acrylate, dimethylaminoalkyl(meth)acrylate, dimethylaminopropyl acrylamide, or acrylamidopropyl trimethyl-ammonium chloride. Percentages above 40% of these monomers will deteriorate the swell capacity of the polymers.

As cross-linking agent all compounds may be used which have at least two ethylenically unsaturated double-bonds or one ethylenically unsaturated double-bond and one functional group reactive towards acid groups, or several functional groups reactive towards acid groups. Examples thereof include: acrylates and methacrylates of polyols, such as butanediol diacrylate, hexanediol dimethacrylate, polyglycol diacrylate, trimethylolpropane triacrylate, or allyl acrylate, diallyl acrylamide, triallyl amine, diallyl ether, methylenebisacrylamide or N-methylolacrylamide.

0 to 30%-wt. partially or completely saponified polyvinyl alcohol, polyvinyl pyrrolidone, starch or starch derivatives, polyglycols, or polyacrylic acids may be comprised as water-soluble polymers in the water-absorbing polymer. The molecular weight of said polymers is not critical provided that they are water-soluble. Preferred water-soluble polymers are starch, polyvinyl alcohol or mixtures of said polymers. The preferred content of said water-soluble polymers in the water-absorbing polymer amounts to about 1 to 5%-wt., in particular if starch and/or polyvinyl alcohol are present as soluble polymers. The water-soluble polymers may be present as graft polymers having the acid-groups-containing polymers.

In addition to polymers obtained by cross-linking polymerization of partially neutralized acrylic acid, those are preferably used which additionally comprise portions of graftpolymerized starch or of polyvinyl alcohol.

There are no specific limitations with respect to the particle shape of the absorber-polymer used. The polymer may be in the form of small spheres obtained by inverse suspension polymerization, or of irregularly shaped particles obtained by drying and pulverizing the gel mass orginiating from the solvent polymerization. Usually, the particle size is between 20 and 2,000 μm, preferably between 50 and 850 μm.

The thermal treatment following the coating is carried out at 150°–250° C., preferably at 170°–200° C. It depends on the residence time and the kind of treating agent. At a temperature of 150° C., the thermal treatment must be carried out for several hours, whereas at 250° C. a few minutes, e.g. 0.5 to 5 minutes, are sufficient to obtain the desired properties. The thermal treatment may be carried out in conventional dryers or ovens, for example, rotary kilns, paddle dryers, disk dryers, or infrared dryers.

The polymers according to the present invention exhibit increased cross-linking and a reduced degree of neutralization in the vicinity of their surfaces.

The polymers according to the present invention may be manufactured on the large scale by continuous or discontinuous processes. The superabsorbers according to the present invention may be used for a variety of applications. If they are used, for example, in sanitary napkins and diapers, or for wound dressing purposes, they have the property of rapidly absorbing large amounts of menstrual blood, urine or other body liquids.

The absorptivity and absorption rate under a simultaneously acting compression load is considerably improved as compared to the starting products. Since the superabsorbers according to the present invention retain the absorbed liquids even under load, they are particularly easy to use. They are preferred to be used at concentrations that— relative to hydrophilic fiber material, such as fluff pulp—are higher than those possible to date; they have excellent absorption properties in constructions comprising 98 to 20%-wt. hydrophilic fibers and 2 to 80%-wt. of the absorbing resin.

The post-treated polymers according to the present invention are used in absorbent articles for various kinds of application, e.g., by mixing with paper, fluff pulp or synthetic fibers, or distributing the agent between substrates made of paper, fluff pulp or non-woven textiles, or by shaping in carriers to form a web.

The superabsorbers obtained according to the described process surprisingly exhibit a considerable improvement in the liquid absorption capacity under load with respect to velocity and total capacity, and, simultaneously, a high gel strength and retention. In particular, an extremely high initial liquid absorption rate under load is achieved so that 80% of the total capacity are achieved after only 15 minutes. The absorption under load, referred to as AUL in DE PS 40 20 780 and EP A 03 39 461, extremely depends on the exerted load. Under a load of 20 g/cm$^2$ (=0.28 psi =19,600 dyn/cm$^2$) the polymers described in the above publications have an absorption capacity for 0.9% sodium chloride solution of 26 to 34 g/g. According to EP A 03 39 461 the absorption capacity of the described polymers under a load of 0.56 psi amounts to a maximum of 13 g/g and under a load of 0.85 psi it amounts to 8 g/g, i.e., at a load of 0.85 psi the subsequently treated polymers absorb a liquid amount which—according to DE PS 40 20 780—corresponds to the amount a water-swellable polymer not treated subsequently absorbs under an increased load.

Under a load of 40 g/cm$^2$ the polymers according to the present invention have an absorption capacity for a 0.9% solution of sodium chloride of at least 15 g/g, preferably above 18 g/g. Under a load of 60 g/cm$^2$ the quantity of absorbed liquid amounts to more than 12 g/g, preferably more than 15 g/g. This is a surprise since, according to DE PS 40 20 780, the amount of secondary treatment agent must be increased from 0.5 to 1.5%-wt. in order to increase the AUL-value (20 g/cm$^2$). However, in particular when water is additionally used to dissolve the alkylene carbonate, this measure results in a wet mixture which can no longer be transported by an air conveyor as well as in excessive emissions during the subsequent thermal treatment.

The manufacturers of textile constructions serving to absorb body liquids endeavor to reduce the large-volume fiber portion and to increase the portion of superabsorber. However, the textile construction must still be capable of retaining the particles, which swell on liquid absorption, in the textile enclosure under load. Since a textile construction for the absorption of body liquids is a highly-porous structure having pores through which a soft swollen gel may pass under load (leakage), it is an object to provide water-swellable polymers having a high load carrying capacity.

The polymers according to the present invention not only have an increased absorption for a 0.9% sodium chloride solution under compression load but also a high absorbency for blood and they provide a faster distribution of the blood within a textile construction under compression load. For that reason the polymers are particularly suitable as absorbent in sanitary napkins, since they have the property of rapidly absorbing body liquids, such as blood, under application of load. The absorption rate for blood under a simultaneously acting compression load is much higher than that of known products.

In a practical test for determining the absorptivity of polymers under load it can be shown that superabsorbers— including the polymers described in EP A 03 39 461— having a high suction power under a load of 20 g/cm$^2$ considerably decrease in swellability under loads of 60 g/cm². In addition, this test shows that water-swellable polymers having the same retention and the same absorptivity under a load of 20 g/cm² may differ in their suction power under an increased load.

Under a load of 20 g/cm² the polymers according to the present invention are capable of withdrawing nearly the same liquid amount from a textile construction as in unloaded condition. This means, for example, that the fluff pulp layer of a diaper loaded by the body of a baby gets dry faster and more reliably and that thus the moisture can be kept away from the skin.

The dynamic pressure increase shown by the water-swellable polymers during the swelling process is called "swelling pressure/load". During swelling said pressure increases until the electrostatic forces in the polymer are in equilibrium with the outer mechanical forces.

The "swelling pressure" of the polymers according to the present invention is up to four times higher than that of commercially available known superabsorbers. Water-swellable polymers having a "swelling pressure" of more than 400 g are preferred, particularly preferred are swellable polymers having a "swelling pressure" of more than 600 g with a swelling area of 4.91 cm².

The polymers according to the present invention are tested as follows:

Test methods

To characterize the water-absorbing polymers, the retention (TB) and the absorption under load (AUL) for 0.9% NaCl-solution were measured, the absorption capacity and rate under load for defibrinated sheep blood were determined.

a) The retention is determined according to the tea bag test method and reported as average value of three measurements. Approximately 200 mg polymer are enclosed in a tea bag and immersed in 0.9% NaCl-solution for 20 minutes. Then the tea bag is centrifuged in a centrifuge (diameter: 23 cm; rpm: 1,400) for 5 minutes and weighed. One tea bag without water-absorbing polymer is used as blank.

$$\text{Retention} = \frac{\text{Weight} - \text{Blank reading}}{\text{Initial weight}} \quad (g/g)$$

b) The absorption of 0.9% NaCl-solution under load (pressure load: 20, 40, 60 g/cm²) is determined according to the method described in EP 03 39 461, page 7:

The initial weight of superabsorber is placed in a cylinder with sieve bottom, the powder is loaded by a piston exerting a pressure of 20, 40 and 60 g/cm². The cylinder is subsequently placed on a Demand-Absorbency-Tester (DAT) and the superabsorber is allowed to suck 0.9% NaCl-solution for one hour.

c) To determine the absorption capacity for blood, about 200 mg polymers are enclosed in a tea bag, immersed in defined sheep blood for 60 minutes and then weighed. The calculation is carried out as under a).

d) On a piece of cellulose fabric having a dimension of 6 cm×20 cm (weight: 48.8 g/m²) 1 g of polymer is evenly spread, then the fabric is covered with a fabric of the same dimension and pressed with 400 g/cm² at 100° C.

The test strip is placed between two glass plates, the upper one having a central bore. A piece of tube having a length of 5.5 cm and an inside diameter of 2.2 cm is glued in said bore. The upper plate is loaded with weights so that a load of 30 g/cm² acts on the test strip. 5 cm³ defibrinated sheep blood having a temperature of 20° C. are dosed into the tube within 30 seconds by means of a flow inducer and the time for seeping in is measured.

e) The determination of the "swelling pressure" Q is carried out by means of the Stevens L.F.R.A. Texture Analyser, C. Stevens & Son Ltd., Laboratory Division, St. Albans AL1 1 Ex Hertfordshire, England.

The glass measuring instrument forming part of the apparatus has a height of 3.5 cm and a diameter of 2.5 cm. Thus the circular surface of the cylinder amounts to 4.91 cm².

0.500 g superabsorber of size fraction 20–50 mesh are weighed into the measuring cylinder having a diameter of 2.7 cm and 10 ml 0.9% NaCl-solution are added. Then the measuring cylinder is brought up by means of a laboratory apparatus until the distance between the lower edge of the measuring instrument and the surface of the sample in the measuring cylinder amounts to 12 min. Through the expansion of the gel, the measuring cylinder is pressed upwards against a two-way load-sensing cell and the load is indicated at the device in grams.

The present invention will be illustrated by the following examples.

EXAMPLES

A) Manufacture of the mixture of polymer A and treatment agent

A powdery polyacrylic acid obtained by polymerization in solution, cross-linked with trimethylolpropane triacrylate and present as sodium salt neutralized to the extent of 70 mol-% was screened to 90 to 850 pm after grinding (polymer A).

TB: 36 g/g; water content: 10.4 %.

Polymer A is continuously fed into a paddle mixer (750 rpm) at 1,000 kg/h and mixed with the treating agent. Subsequently, the mixture is transferred to a conveyor and transported to a storage vessel. The appearance and behavior during transport and storage of the solid-liquid-mixture is judged.

| Examples | Treatment Agent | | | Solid-Liquid-Mixture | |
| --- | --- | --- | --- | --- | --- |
| | % | % | % | Appearance | Behavior |
| Comparison 1 | 0.5 EC | 0.5 H₂O | — | dry | free-flowing |
| Comparison 2 | 1.0 EC | 1.0 H₂O | — | wet | formation of lumps |
| Comparison 3 | 0.25 EC | 0.25 H₂O | — | dry | free-flowing |
| Comparison 4 | 0.5 Gl | 0.5 H₂O | — | wet | formation of lumps |
| Comparison 5 | 0.25 Gl | 0.25 H₂O | 1.0 Et | wet | free-flowing |

-continued

| Examples | Treatment Agent % | % | % | Solid-Liquid-Mixture Appearance | Behavior |
|---|---|---|---|---|---|
| Example 1 | 0.1 EC | 1.0 H$_3$PO$_4$ | — | dry | free-flowing |
| Example 2 | 0.1 Gl | 0.6 H$_3$PO$_4$ | 0.3 H$_2$O | dry | free-flowing |

EC: ethylene carbonate
Gl: glycerol
H$_3$PO$_4$: phosphoric acid 85%
Et: ethanol
Comparisons 1 to 3 correspond to DE-PS 40 20 780; comparisons 4 and 5 correspond to DE-OS 35 23 617.

B) Heating the mixtures of polymer A and the treatment agents 90 kg/h of the free-flowing, i.e. easy to handle, mixtures obtained according to A) are continuously dosed into a paddle dryer heated by vapor having a temperature of 180° C. The dryer has a working volume of 40 l. The amount of purge air to lead off the vapors amounts to about 50 m$^3$/h.

The characteristic values of the powdery polymers obtained and the organic substances in the exhaust gas -indicated as organic carbon (TOC)—are listed in Table 2.

TABLE 2

| Example | Mixture of Example | TB [g/g] | AUL 20 g/cm$^2$ [g/g] | TOC [g/h] |
|---|---|---|---|---|
| Comparison 6 | Comparison 1 | 32 | 30 | 115 |
| Comparison 7 | Comparison 3 | 33 | 24 | 44 |
| Comparison 8 | Comparison 5 | 32 | 31 | 320*) |
| Example 3 | Example 1 | 32 | 30 | 14 |
| Example 4 | Example 2 | 31 | 30 | 4 |

*)Part of the ethanol evaporates during mixing and conveying.

C) Manufacture of the mixture of polymer B and treatment agent

The polymer obtained by polymerizing a 30% aqueous acrylic acid, which was present as sodium salt neutralized to the extent of 65 mol-%, in the presence of 0.28%-wt. triallyl amine and 3.5%-wt. polyvinyl alcohol, is dried in a stream of hot air at 160° C., ground and sieved to 120 to 850 μm (polymer B). TB: 37 g/g; water content: 10.5%; SP: 11.8%.

Like polymer A, polymer B is continuously mixed with 1.2%-wt. of a solution having a temperature of 40° C. and consisting of 0.2 parts dimethylolpropionic acid and 1 part 85% phosphoric acid and intermediately ensilaged.

D) Heating the mixture according to C)

By means of an air conveyor the free-flowing mixture obtained in C) is fed into a dryer equipped with disk-shaped rotating mixing elements heated by vapor of 184° C. Subsequently, the mixture is cooled in fluidized bed. The product data and TOC-values are listed in Table 3.

TABLE 3

| Example | Through- put [kg/h] | TB [g/g] | AUL [g/g] at 20 g/cm$^2$ | 40 g/cm$^2$ | 60 g/cm$^2$ | TOC [g/h] | SP [%]* |
|---|---|---|---|---|---|---|---|
| 5 | 90 | 32 | 31 | 18 | 14 | 4.5 | 6.7 |
| 6 | 80 | 30 | 30 | 20 | 18 | 5.0 | — |
| 7 | 70 | 28 | 28 | 26 | 23.5 | — | 4.2 |

*)SP: Soluble portions, determined according to EP A 02 05 674.

TABLE 4

Determination of the absorption capacity and rate for blood

| Example | Polymers | Ab- sorption [g/g] | Absorption rate at 30 g/cm$^2$ load [min] |
|---|---|---|---|
| 8 | from Ex. 3 | 37.5 | 4.5 |
| Comparison 9 | FAVOR SAB*)FAM | 44 | >30 |

*)Manufacturer: Chemische Fabrik Stockhausen, Krefeld, FRG

Determination of the polymer absorbency from a matrix

A round fluff pad having a diameter of 6 cm and a weight of 2 g and lying in a Petri dish is soaked with different amounts of 0.9% NaCl-solution. 0.20 g polymers are weighed into a cylinder of plexiglass having an inside diameter of 25.8 mm and a sieve fabric at the bottom (mesh width 36 μm) and loaded with a punch having a diameter of 25 mm and a weight of 106 g. The cylinder group (cylinder, polymers, punch)is weighed (A) and placed in the center of the moist pad. After one hour, the cylinder group is reweighed (B).

$$\text{Absorbency} = \frac{B - A}{0.20} \text{ g/g}$$

TABLE 5

| Example 9 | | Comparison 10 | |
|---|---|---|---|
| Polymer acc. to Ex. 6 | | Polymer acc. to comp. 1 | |
| TB [g/g]: | 30 | TB [g/g]: | 32 |
| AUL 20 g/cm$^2$ [g/g]: | 30 | AUL 20 g/cm$^2$ [g/g]: | 30 |
| AUL 60 g/cm$^2$ [g/g]: | 18 | AUL 60 g/cm$^2$ [g/g]: | 10 |

| Solution of sodium chloride in pad [g] | Amount of NaCl-solution absorbed by the polymer [g/g] | |
|---|---|---|
| 7.5 | 14.0 | 10.0 |
| 15.0 | 20.5 | 13.1 |
| 22.5 | 25.0 | 17.6 |
| 30.0 | 28.9 | 20.3 |

TABLE 6

Determination of the "swelling pressure"

| Time [min] | 2 | 3 | 5 | 10 | 15 |
|---|---|---|---|---|---|
| Polymer of Example 7 | 200 | 410 | 520 | 820 | 825 |
| FAVOR SAB 800[1] | 195 | 240 | 250 | 260 | 260 |

[1]Manufacturer: Chemische Fabrik Stockhausen GmbH, Krefeld, FRG

We claim:

1. A powdery polymer composition which is capable of absorbing aqueous or serous liquids and blood comprising:
   (A) a cross-linked polymer formed of:
      a) 55–99.9%-wt. polymerized unsaturated, polymerizable acid-groups-comprising monomers which are neutralized to the extent of at least 25 mol-%,
      b) 0–40%-wt. polymerized unsaturated monomers which are copolymerizable with a), and
      c) 0.1–5.0%-wt. of a cross-linking agent, and
   (B):
      d) 0–30%-wt. of a water-soluble polymer, the weight amounts of a) to d) being based on said cross-linked polymer, wherein 100 parts of particles of said polymer composition is mixed with at least 0.1 and not more than 10 parts by weight of an at least 10% by weight aqueous solution of phosphoric acid, and
      e) 0.05–0.3 parts by weight, based on said polymer composition, of a compound capable of reacting with at least two carboxyl groups and not comprising an alkali-salt-forming group in the molecule, and/or
      f) 0.05–1 parts by weight, based on said polymer composition, of a compound capable of reacting with at least two carboxyl groups and comprising an alkali-salt-forming group in the molecule,
   and heated to 150°–250° C.

2. The polymer composition of claim 1, having
   a) a retention of 27 to 34 g of 0.9% sodium chloride solution per gram of polymer,
   b) an absorption for 0.9% solution of sodium chloride under a load of 40 g/cm$^2$ of more than 15 g per gram of polymer,
   c) an absorption for 0.9% solution of sodium chloride under a load of 60 g/cm$^2$ of more than 12 g per gram of polymer, and
   d) a swelling pressure of more than 400 g.

3. The polymer composition of claim 1, wherein said polymerizable acid-groups-comprising monomers are selected from the group consisting of acrylic acid, methacrylic acid and 2-acrylamido-2-methylpropane sulfonic acid.

4. The polymer composition of claim 1, wherein said acid-groups-comprising monomers are neutralized to the extent of at least 50 mol-%.

5. The polymer composition of claim 1, wherein said polymerizable acid-groups-comprising monomers consist of acrylic acid, neutralized to the extent of 50–80 mol-%.

6. The polymer composition of claim 1, wherein said water-soluble polymer is used at a concentration of 1 to 5%-wt.

7. The polymer composition of claim 1, wherein said water-soluble polymer is starch and/or polyvinyl alcohol.

8. A process for the production of a powdery polymer composition capable of absorbing aqueous or serous liquids and blood comprising:
   (A) a cross-linked polymer formed of:
      a) 55–99.9%-wt. polymerized unsaturated, polymerizable acid-groups-comprising monomers which are neutralized to the extent of at least 25 mol-%.
      b) 0–40%-wt. polymerized unsaturated monomers which are copolymerizable with a), and
      c) 0.1–5.0%-wt. of a cross-linking agent, and
   (B)
      d) 0–30%-wt. of a water-soluble polymer, the weight amounts of a) to d) being based on said cross-linked polymer, comprising mixing 100 parts of of particles of said polymer composition with at least 0.1 and not more than 10 parts by weight of an at least 10% by weight aqueous solution of phosphoric acid and
      a) 0.05–0.3 parts by weight, based on said polymer composition, of a compound capable of reacting with at least two carboxyl groups and not comprising an alkali-salt-forming group in the molecule, and/or
      b) 0.05–1 parts by weight, based on said polymer composition, of a compound capable of reacting with at least two carboxyl groups and comprising an alkali-salt-forming group in the molecule, and heating to 150°–250° C.

9. A textile having improved absorption of body liquids under an increased load, said textile comprising a polymer composition according to claim 1, wherein said textile has
   a) a retention of 27 to 34 g of 0.9% sodium chloride solution per gram of polymer,
   b) an absorption for 0.9% solution of sodium chloride under a load of 40 g/cm$^2$ of more than 15 g per gram of polymer,
   c) an absorption for 0.9% solution of sodium chloride under a load of 60 g/cm$^2$ of more than 12 g per gram of polymer, and
   d) a swelling pressure of more than 400 g.

10. The textile of claim 9, wherein said textile comprises hydrophilic fibers and 2–80%-wt. of said polymer, relative to the total weight of said textile.

11. The polymer composition of claim 2, wherein said polymer has an absorption for 0.9% solution of sodium chloride under a load of 40 g/cm$^2$ of more than 18 g.

12. The polymer composition of claim 2, wherein said polymer has an absorption for 0.9% solution of sodium chloride under a load of 60 g/cm$^2$ of more than 15 g.

13. The polymer composition of claim 2, wherein said polymer has a swelling pressure of more than 600 g.

14. The textile of claim 9, wherein said textile has an absorption for 0.9% solution of sodium chloride under a load of 40 g/cm$^2$ of more than 18 g.

15. The textile of claim 9, wherein said textile has an absorption for 0.9% solution of sodium chloride under a load of 60 g/cm$^2$ of more than 15 g.

16. The textile of claim 9, wherein said textile has a swelling pressure of more than 600 g.

* * * * *

UNITED STATES PATENT AND TRADEMARK OFFICE
CERTIFICATE OF CORRECTION

PATENT NO. : 5,610,220
DATED : March 11, 1997
INVENTOR(S) : Helmut KLIMMEK, et al.

It is certified that error appears in the above-indentified patent and that said Letters Patent is hereby corrected as shown below:

On the title page, item [87], the PCT publication information should read:

--[87]   PCT Pub. No.:      WO94/15651

PCT Pub. Date:     Jul. 21, 1994--

Signed and Sealed this

Twenty-second Day of July, 1997

Attest:

BRUCE LEHMAN

*Attesting Officer*   *Commissioner of Patents and Trademarks*